United States Patent
Cho et al.

(10) Patent No.: US 8,086,301 B2
(45) Date of Patent: Dec. 27, 2011

(54) METHOD AND APPARATUS FOR CUFFLESSLY AND NON-INVASIVELY MEASURING WRIST BLOOD PRESSURE IN ASSOCIATION WITH COMMUNICATION DEVICE

(75) Inventors: Jae-Geol Cho, Yongin-si (KR); Sun-Tae Jung, Anyang-si (KR); Jae-Joong Im, Jeonju-si (KR)

(73) Assignee: Samsung Electronics Co., Ltd., Maetan-dong, Yeongtong-gu, Suwon-si, Gyeonggi-do (KR)

( * ) Notice: Subject to any disclaimer, the term of this patent is extended or adjusted under 35 U.S.C. 154(b) by 436 days.

(21) Appl. No.: 12/075,377

(22) Filed: Mar. 11, 2008

(65) Prior Publication Data

US 2008/0228089 A1    Sep. 18, 2008

(30) Foreign Application Priority Data

Mar. 12, 2007    (KR) .......................... 10-2007-0024163

(51) Int. Cl.
*A61B 5/04*    (2006.01)

(52) U.S. Cl. ...................................... 600/513
(58) Field of Classification Search .................. 600/509, 600/513, 516, 517
See application file for complete search history.

(56) References Cited

U.S. PATENT DOCUMENTS

| | | | | |
|---|---|---|---|---|
| 5,033,471 A | | 7/1991 | Yokoe et al. | 128/681 |
| 5,535,753 A | * | 7/1996 | Petrucelli et al. | 600/485 |
| 6,361,501 B1 | * | 3/2002 | Amano et al. | 600/500 |
| 6,413,223 B1 | | 7/2002 | Yang et al. | 600/485 |
| 6,669,648 B1 | | 12/2003 | Fortin et al. | 600/490 |
| 2007/0021676 A1 | | 1/2007 | Han et al. | |

FOREIGN PATENT DOCUMENTS

| | | |
|---|---|---|
| JP | 2006-149846 | 6/2006 |
| KR | 2005-67651 | 7/2005 |
| KR | 2007-75515 | 7/2007 |
| WO | WO 2004/019754 | 3/2004 |

OTHER PUBLICATIONS

Im, Jae J.; et al.; "A Study for the Development of a Noninvasive Continuous Blood Pressure Measuring System by Analyzing Radial Artery Pulse From a Wrist;" Engineering in Medicine and Biology Society; Sep. 1995; XP 010215080.

* cited by examiner

*Primary Examiner* — Brian T Gedeon
(74) *Attorney, Agent, or Firm* — Cha & Reiter, LLC (57) ABSTRACT

A method of cufflessly and non-invasively measuring blood pressure in a wrist region of a patient in association with a communication device that relays the information being measured includes: detecting a magnitude difference between a plurality of pulse wave signals detected from a wrist of a user; detecting feature points from an electrocardiogram (ECG) and pulse wave signals detected from the user; extracting variables needed to calculate the highest blood pressure and the lowest blood pressure using the detected feature points; and calculating the highest blood pressure and the lowest blood pressure of the user by deducing a scatter diagram using the extracted variables.

11 Claims, 12 Drawing Sheets

METHOD AND APPARATUS FOR CUFFLESSLY AND NON-INVASIVELY MEASURING WRIST BLOOD PRESSURE IN ASSOCIATION WITH COMMUNICATION DEVICE

CLAIM OF PRIORITY

This application claims the benefit of priority under 35 U.S.C. §119(a) from a Patent Application filed in the Korean Intellectual Property Office on Mar. 12, 2007 and assigned Serial No. 2007-24163, the contents of which are incorporated herein by reference in its entirety.

BACKGROUND OF THE INVENTION

1. Field of the Invention

The present invention relates to the use of a pulse wave generated around an artery of a human body. More particularly, the present invention relates to a method and apparatus for acquiring a pulse wave signal and an electrocardiogram (ECG) signal using a pressure sensor, an infrared sensor, and an electrode and providing an analyzed result as a blood pressure value of an artery of a brachium.

2. Description of the Related Art

The occurrence of diseases related to high blood pressure such as heart disease and strokes has been shown to increase with a decrease of physical activity and a correlation with certain dietary habits. On the other hand, one of reasons that the importance of preventing diseases related to high blood pressure in society is that the occurrence of diseases related to high blood pressure rapidly increases with an increase in age. One of the methods of diagnosing and preventing the occurrence of diseases related to high blood is to periodically measure blood pressure. Arterial blood pressure is determined by the flow of blood, the elasticity of a blood vessel, contraction resistance, etc., and is a vital sign indicating an abnormal symptom in organs related to high blood pressure. High blood pressure can damage all major organs in the body.

There are two basic methods of measuring blood pressure, i.e. an invasive method and a non-invasive method. When a high-risk patient is being treated in an Operating Room (OR) or an Intensive Care Unit (ICU), the invasive method, which can continuously monitor arterial blood pressure and take an arterial blood sample on demand for analyzing gas of the arterial blood, is used. However, the invasive method is very cumbersome in preparation and treatment, may cause a complication such as damage to tissues due to infection or blood vessel obstruction. In addition, as the invasive method, is mostly applied to critically ill patients, and patient management in such cases requires a great deal of care use, there is a concern regarding complications associate with use of the invasive method. Thus, under ordinary circumstances, the non-invasive method of measuring blood pressure using a cuff is mainly used. However, the non-invasive method has disadvantages that blood pressure cannot be continuously monitored, a difference may occur according to subjectivity of the person taking the measurement, etc. Also, there is difficulty in measuring blood pressure in the case where the blood pressure decreases to less than a predetermined value. For example, it has been reported that it is difficult to apply the non-invasive method to children and critically ill patients, and accuracy of the non-invasive method is significantly lower for patients having diastolic blood pressure of 70 mm Hg.

In addition, there is another disadvantage in that correct blood pressure measurements cannot be obtained if the circumference of a brachium wrapped by a cuff is not factored into a blood pressure measurement using a cuff. However, at present, it is impossible to measure blood pressure with a cuff and factor in the circumference of a brachium. Moreover, since a process of applying pressure of around 200 mmHg is necessary when a cuff is used, a blood vessel or tissue may be damaged from the pressure. In order to compensate these disadvantages due to a cuff, there have been unsuccessful attempts to continuously measure blood pressure via a non-invasive method without the use of the cuff. However, reliable blood pressure monitoring under such circumstances has not been realized.

Attempts at providing apparatuses for continuously measuring non-invasive and cuffless blood pressure are disclosed in U.S. Pat. No. 6,413,223 titled "Cuffless Continuous Blood Pressure Monitor" and U.S. Pat. No. 6,669,648 titled "Continuous Non-invasive Sphygmo-manometer". However, such measured positions are limited to a finger, or blood pressure is measured at a position around a wrist, which is difficult to affix. Moreover, since such as the apparatus as disclosed in the aforementioned patent requires additional devices for driving a light source to continuously measure blood pressure, such apparatuses fail to solve a problem that it is inconvenient and difficult to apply the such apparatuses to a human body in order to make an accurate measurement.

As the measurement of blood pressure provides important diagnostic information and is a factor in the treatment of patients for many illnesses, there is a long-felt need in the art to develop a technique of simply and continuously measuring blood pressure at a wrist without using a cuff. There are many obstacles that must be overcome, such as the deployment of a sensor attached to the human body, the establishment of a correct algorithm for calculating blood pressure values using a waveform of a pulse wave, easy attachment and detachment of such an apparatus, and portability.

SUMMARY OF THE INVENTION

The present invention has been made in part to solve in part at least some of the above problems and/or disadvantages described above, and to provide at least the advantages discussed herein below. Accordingly, an aspect of the present invention is to provide an apparatus for providing and storing non-invasive continuous blood pressure values so as to provide continuous blood pressure measurement by establishing an algorithm for acquiring a waveform of a pulse wave generated at a specific arterial region of a human body. The invention, in an exemplary embodiment, may include an output from an infrared sensor, an electrocardiogram signal, and processing a detected pulse wave using a pressure sensor, the infrared sensor, and an electrode.

In addition, the aforementioned exemplary aspect of the invention includes application of a pulse wave sensing system for considerably improving erroneous measurements associated with conventional blood pressure measurement apparatuses that does not use a cuff. In addition, in the present invention reliability can be increased by applying an accurate waveform detecting method that takes into consideration various conditions of the environment in which it is used. In particular, the present invention provides in increased reliability can by applying an algorithm for calculating correct blood pressure values. Also, the present invention permits the performance of self-health management at any time by conveniently putting on the pulse wave sensing system on a wrist, and continuous blood pressure monitoring can be performed in hospitals without troubling the patients.

According to an exemplary embodiment of the present invention, a cuffless non-invasive continuous blood pressure measurement apparatus, which improves the above-described problems, typically includes a signal detector, a pulse wave signal analyzer, a pulse wave signal display unit, an interface unit, and a power supply unit. The signal detector includes a sensor unit converting more than one of an infrared sensor output signal, a pulse wave signal, and an electrocardiogram (ECG) signal detected from a wrist arterial region into analog signals and outputting the analog signals. The pulse wave signal analyzer converts the pulse wave signal, which was an analog signal processed by the signal detector, into a digital signal, and the pulse wave signal display unit displays a continuous blood pressure value of a brachium artery from the digitized pulse wave signal. The interface unit takes charge of data communication with an external device, and the power supply unit supplies power to the measurement apparatus.

According to another exemplary aspect of the present invention, there is provided a method of cufflessly and non-invasively measuring blood pressure at a person's wrist, which, in association with a communication device, the method comprising: detecting a magnitude difference between more than one pulse wave signals detected from a wrist of a user; detecting feature points from electrocardiogram (ECG) and pulse wave signals detected from the user; extracting variables needed to calculate the highest blood pressure and the lowest blood pressure using the detected feature points; and calculating the highest blood pressure and the lowest blood pressure of the user by deducing a scatter diagram using the extracted variables.

According to yet another exemplary aspect of the present invention, there is provided an apparatus for cufflessly and non-invasively measuring blood pressure at a person's wrist in association with a communication device, the apparatus comprising: a sensor unit for measuring necessary electrocardiogram (ECG) and pulse wave signals from a user; a controller for controlling the measured signals; and a display unit for displaying the controlled signals to the user.

BRIEF DESCRIPTION OF THE DRAWINGS

The above and other exemplary objects, features and advantages of the present invention will become more apparent from the following detailed description when taken in conjunction with the accompanying drawing in which.

DETAILED DESCRIPTION OF THE INVENTION

Preferred exemplary embodiments of the present invention will be described herein below with reference to the accompanying drawings. It will be understood by those skilled in the art that specific factors, such as detail regarding some specific components, described herein below is being provided only for assistance in the general understanding of the present invention by a person of ordinary skill in the art, and the invention is not limited to the examples shown and described herein. Various changes in form and details may be made therein without departing from the spirit of the invention and the scope of the appended claims. Hereinafter, a configuration and an operation of a non-invasive continuous blood pressure measurement apparatus according to an exemplary embodiment of the present invention and a non-invasive continuous blood pressure measurement method performed by the apparatus will be described in detail with reference to the attached drawings.

It is to be understood that the term "wrist blood pressure" refers to a measurement made in the region of the wrist. It should also be understood that the forearm could also be considered as being within such a region.

Figure 1:
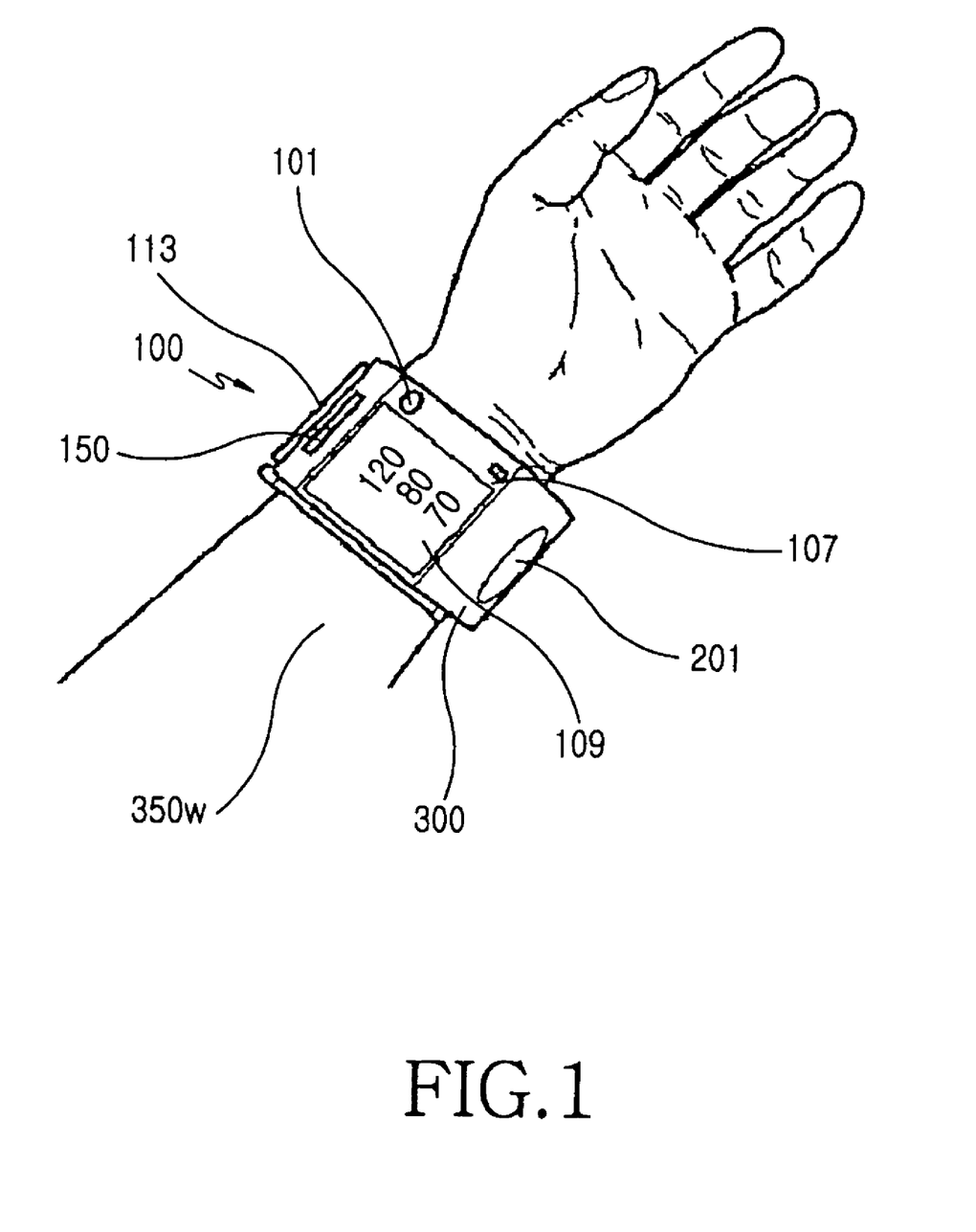
FIG. 1 is a perspective view of an apparatus for cufflessly and non-invasively measuring blood pressure at a person's wrist according to an exemplary embodiment of the present invention.

FIG. 1 is a perspective view of an apparatus for cufflessly and non-invasively measuring wrist blood pressure according to an exemplary embodiment of the present invention. Referring to FIG. 1, the reference numeral 100 denotes the total configuration of a portable continuous blood pressure measurement apparatus 300 according to an exemplary embodiment of the present invention. The non-invasive continuous blood pressure measurement apparatus 300 adapted for arrangement on a wrist region of a user, and the apparatus 300 is typically driven via a measurement button 101. A normal or abnormal operation state is displayed by a state display Light Emitting Diode (LED) 107. Continuous blood pressure measured using the apparatus 300 is displayed by a display unit 109 of the apparatus 300. Signals measured using the apparatus 300 are a pulse wave signal, an infrared signal for measuring light intensity through incidence and reflection thereof, and an ECG signal, and in order to measure the ECG, the ECG measurement unit 201 measures an ECG of a user via a finger arranged thereon.

In addition, in order to detect a pulse wave, a pressure and position are adjusted using a wristband 113 of the apparatus 300. The continuous blood pressure measured using the apparatus 300 can be transmitted to a cellular phone or other communication device via a communication terminal 150.

In order to measure continuous blood pressure using the portable continuous blood pressure measurement apparatus 300, the apparatus 300 is switched to a measurement mode by pushing the measurement button 101, which in this case is arranged in the upper right side of the apparatus 300. A sensor unit (200 shown in FIG. 2) is typically disposed near a radial artery region (350a shown in FIG. 3) of a wrist 350w, and the apparatus 300 is adapted for arrangement around or in the region of the wrist 350w of the user using the wristband 113 of the apparatus 300. It is determined through the status display LED 107 of the fixed apparatus 300 whether a pulse wave signal is being stably detected, and in order to measure the stable pulse wave signal, the stable pulse wave is measured by adjusting pressure applied to the sensor unit (200 shown in FIG. 2). An ECG signal is measured by contact of a finger of the other hand, which is free from the apparatus 300, with an ECG sensor 201 of the apparatus 300. The measured pulse wave and ECG signal are stored in a Random Access Memory (RAM) (455 of FIG. 4) included in a controller (450 of FIG. 4) of the apparatus 300. After the stored data is calculation-processed through the process illustrated in FIG. 7 to be described later, a continuous blood pressure value is displayed on the display unit 109.

FIG. 2 shows two exemplary types of the sensor unit 200 of a continuous blood pressure measurement apparatus according to an exemplary embodiment of the present invention. FIGS. 2A and 2B respectively illustrate a front view and a side view of the sensor unit 200 of the apparatus 300 illustrated in FIG. 1 according to an exemplary embodiment of the present invention, wherein the sensor unit includes a pressure sensor and an ECG sensor, and FIGS. 2C and 2D respectively show a front view and a side view of the sensor unit 200 of the apparatus illustrated in FIG. 1, which includes an optical sensor, according to another exemplary embodiment of the present invention, in which the sensor unit includes a pressure sensor, an ECG sensor, and an optical sensor.

Figure 2A:
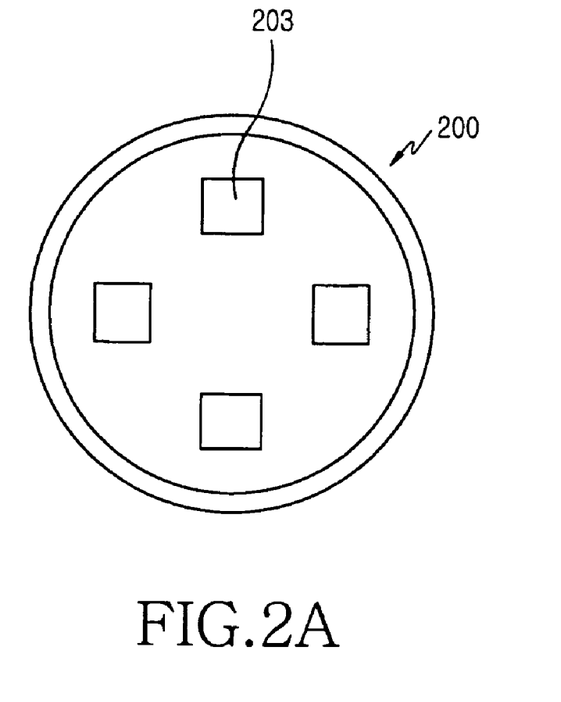
FIGS. 2A and 2B are respectively a front view and a side view of a sensor unit of the apparatus illustrated in FIG. 1 according to an exemplary embodiment of the present invention.
Figure 2B:
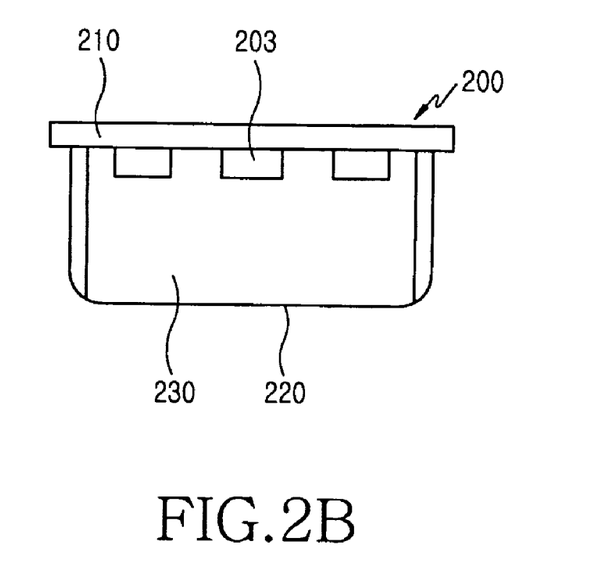

Referring now to FIGS. 2A and 2B, the sensor unit 200 typically includes more than one pressure sensor 203, a Printed Circuit Board (PCB) 210 to which the pressure sensors 203 are arranged, a gel type epoxy processed unit 220 that typically surrounds the sensors 203 and the PCB 210, and a portion filled with gel 230. Each pressure sensor 203 used in the present invention converts a pressure signal to an electrical signal and measures a pressure of blood flowing through a blood vessel, which is affected to the blood vessel, by being put on a radial artery. The more than one pressure sensors 203 are arranged on the PCB 210, and in order to prevent the gel of a portion to which pressure of the pressure sensors 203 in a vessel of the sensor unit 200 is applied from leaking out and changing the overall the density of the gel 230 in the vessel of the sensor unit 200, the gel 230 of a portion of the sensor unit 200 touched to the wrist 350w of the user is processed by the epoxy processed unit 220. Since the gel 230 is used as a transmitter for transmitting a pulse wave signal, a pulse wave signal transmitted to each pressure sensor 203 varies according to density and a configuration of the gel 230.

A pulse wave signal transmitted to each pressure sensor 203 varies according to an angle and pressure achieved between the radial artery region (350a of FIG. 3) of the user and the sensor unit 200, and the magnitude of each pulse wave signal output from the more than one pressure sensors 203 varies according to an amount of pressure applied to the wrist 350w. This variation output by the more than one pressure sensors is used to correct the magnitude of a detected pulse wave to absolute pressure, the absolute pressure is processed by a calculation algorithm, and a calculated signal is used for continuous blood pressure analysis.

Thus, according to an exemplary aspect of the present invention, the sensor unit 200 for selecting a correct position of an artery and extracting a clear pulse wave signal preferably typically includes at least one pressure sensor 203, and outputs such pressure sensors 203, an ECG signal detected from an electrode installed in a wrist strap, and a pulse wave signal can be used for accurate and highly repeatable continuous blood pressure analysis.

Figure 2C:
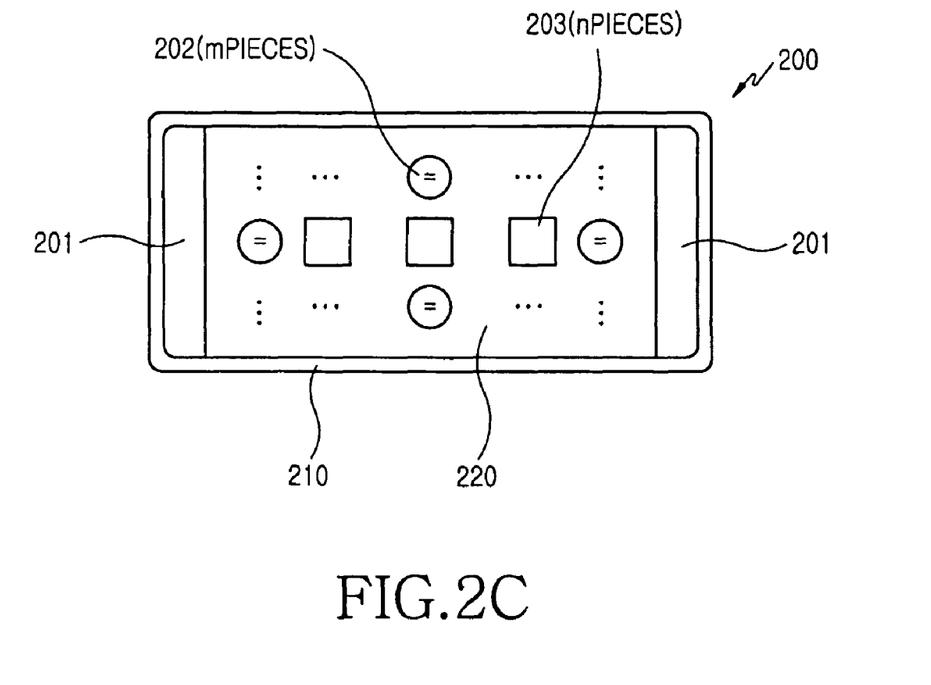
FIGS. 2C and 2D are respectively a front view and a side view of the sensor unit of the apparatus illustrated in FIG. 1, which includes an optical sensor, according to another exemplary embodiment of the present invention.
Figure 2D:
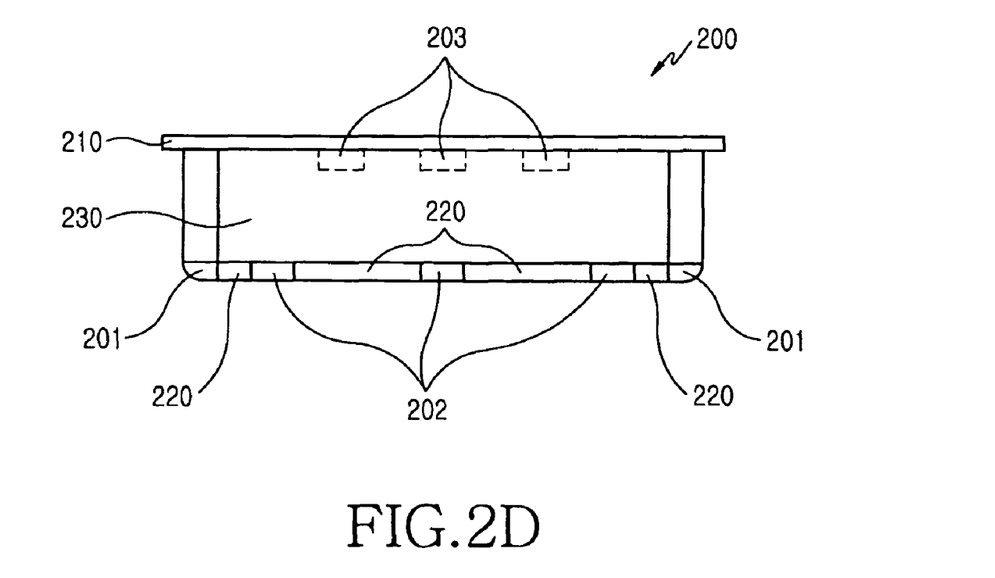

Referring now to FIGS. 2C and 2D corresponding to another exemplary embodiment of the present invention, the sensor unit 200 includes an ECG sensor 201, a plurality of infrared sensors 202, a plurality of pressure sensors 203, a PCB 210 to which the pressure sensors 203 are fixed, a gel type epoxy processed unit 220 surrounding the infrared sensors 202.

Figure 4:
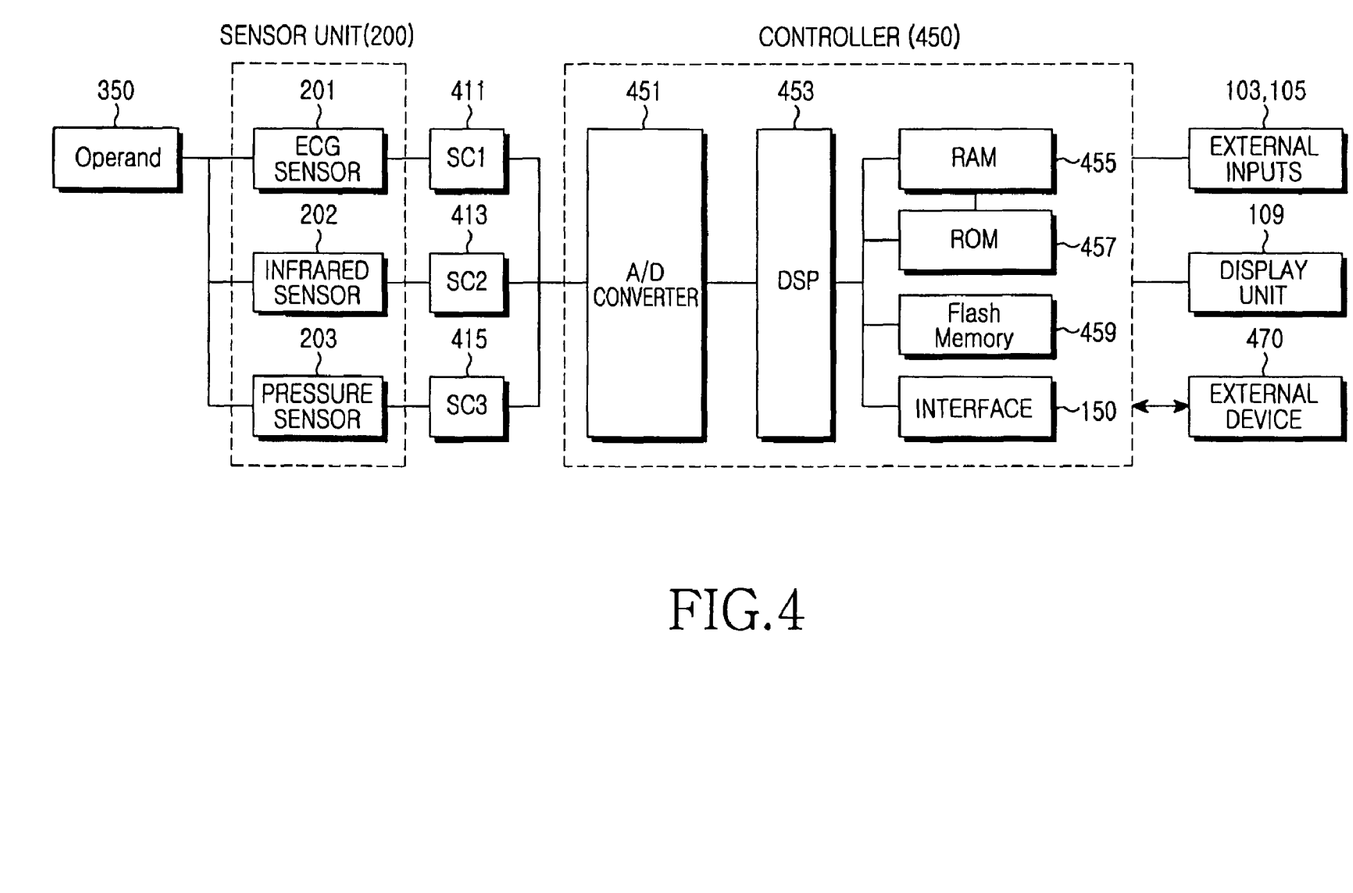
FIG. 4 is a conceptual diagram of a blood pressure measurement apparatus according to an exemplary embodiment of the present invention.

Still referring to FIGS. 2C and 2D, according to this exemplary embodiment of a sensor unit 200 of the present invention, the ECG sensor 201 detects an ECG signal indicating electrical activity of a heart and transmits the ECG signal to an analog signal processing unit (411 shown in FIG. 4). In the case of the exemplary embodiment of FIGS. 2A and 2B, since three ECG sensors including the electrode (201 of FIG. 1) located in the outside of the apparatus 300 are typically used, two additional electrodes are typically used in a strap region. In the case of the exemplary embodiment of FIGS. 2C and 2D, two electrodes in the sensor unit 200 and the electrode (201 of FIG. 1) located in the outside of the apparatus 300 are used to acquire the ECG signal.

Figure 2E:
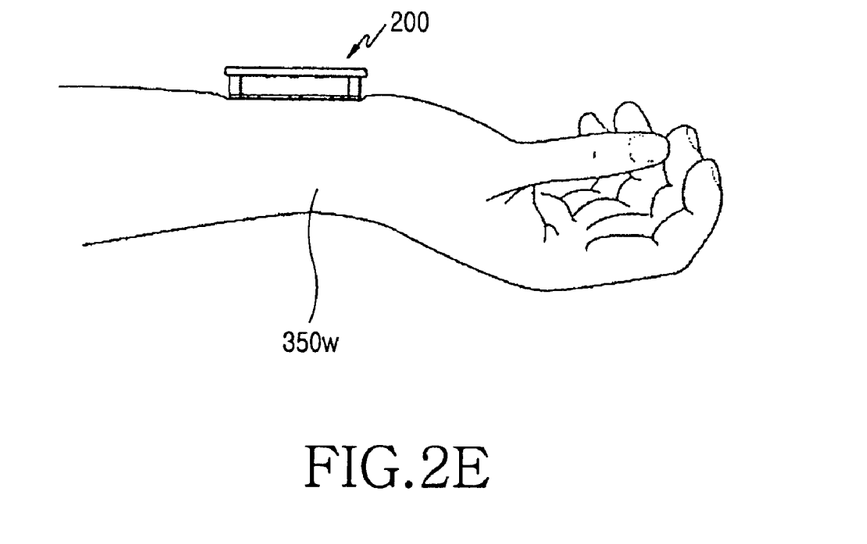
FIG. 2E is a side view of the sensor unit of the apparatus illustrated in FIG. 1, which is put on a wrist, of a user, according to an exemplary embodiment of the present invention.

The infrared sensor 202 typically includes a photo diode and an LED, and light emitted by the LED is multiply diffused through the skin, subcutaneous fat, muscles, and a radial artery around the wrist 350w of the user and received by the photo diode, generating an analog output signal. The infrared sensors 202 of the sensor unit 200 according to an exemplary embodiment of the present invention are typically located around a group of the pressure sensors 203, and an output signal of each infrared sensor 202 is processed by a calculation program of the controller (450 shown in FIG. 4), forming a vector component. FIG. 2E is a side view of a sensor unit of the apparatus 300 illustrated in FIG. 1, which is put on a wrist of a user, according to an exemplary embodiment of the present invention.

Figure 3:
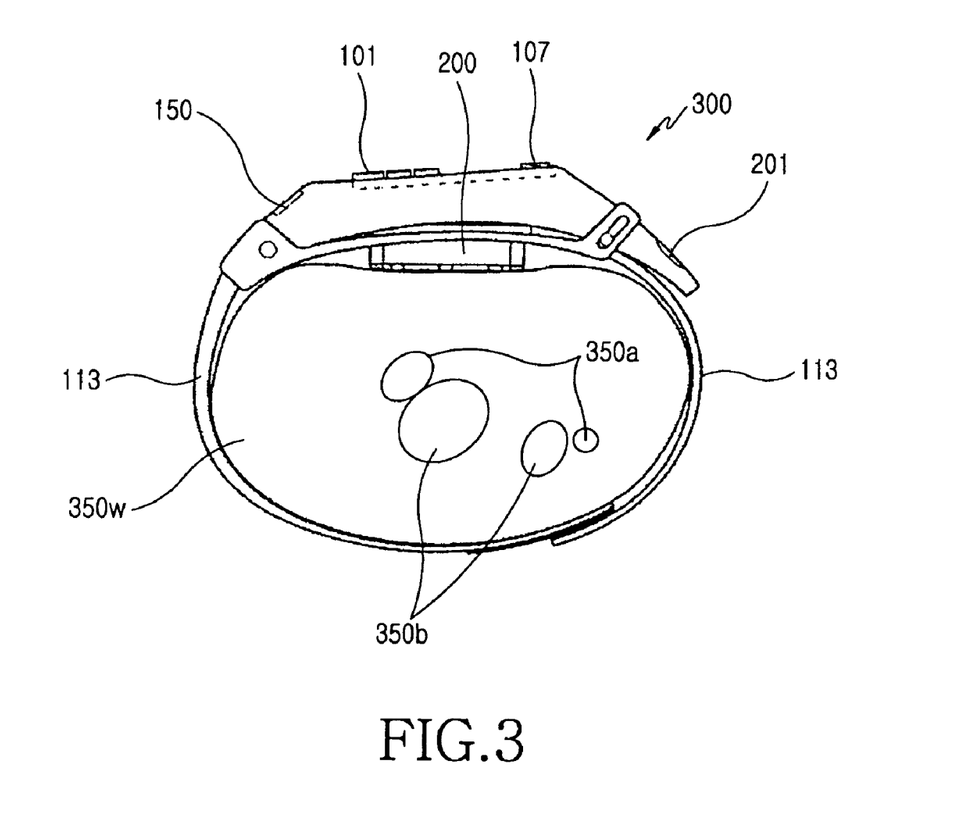
FIG. 3 is a side view of an apparatus for cufflessly and non-invasively measuring blood pressure at a person's wrist according to an exemplary embodiment of the present invention.

FIG. 3 is a side view of an apparatus for cufflessly and non-invasively measuring wrist blood pressure according to an exemplary embodiment of the present invention. FIG. 3 shows an exemplary configuration of the continuous blood pressure measurement apparatus and includes the configuration illustrated in FIG. 1. The configuration of the apparatus will now be described. The non-invasive continuous blood pressure measurement apparatus 300 is put on around the wrist region 350w of the user and operated using the measurement button 101, and a normal or abnormal operating state is displayed by the status display LED 107. Continuous blood pressure that is measured using the apparatus 300 is displayed by the display unit 109 of the apparatus 300. Signals measured using the apparatus 300 are a pulse wave signal, an infrared signal for measuring light intensity through incidence and reflection thereof, and an ECG signal, and in order to measure the ECG, the user 350 typically arranges a finger on the ECG sensor unit 201.

In addition, in order to detect a normal pulse wave, pressure and position of the sensor unit 200 applied to the artery region 350a passing through a radial bone 350b of the wrist 350w of the user are adjusted using the wristband 113. The continuous blood pressure measured using the apparatus 300 can be transmitted via the terminal 150 of a communication device in order to communicate with an external device (470 shown in FIG. 4).

FIG. 4 is a conceptual diagram of a blood pressure measurement apparatus according to an exemplary embodiment of the present invention.

Referring to FIG. 4, a pulse wave signal is measured using the ECG sensor 201, at least one infrared sensor 202 for measuring a correct pulse wave signal, and at least one pressure sensor 203 from the operand 350 corresponding to the user. An ECG signal measured using the ECG sensor 201 is filtered and amplified by the analog signal processing unit corresponding to an SC1 411. The analog signal processed ECG signal is then input to an analog input terminal of an Analog/Digital (A/D) converter 451 of the controller 450, converted to a digital signal, and stored in the RAM 455.

Each infrared sensor signal, which is measured using the at least one infrared sensor 202, is filtered and amplified by an analog signal processing unit corresponding to an SC2 413. This analog signal processed infrared sensor signal is input to the analog input terminal of the A/D converter 451 of the controller 450, converted to a digital signal, digital signal processed by a Digital Signal Processor (DSP) 453 using a position and depth analysis program stored in a Read Only Memory (ROM) 457, and displayed on the display unit 109.

The infrared sensor signal is used to compensate individual conditions varying according to a user, such as a measured position and the depth of an artery. A pulse wave signal measured using a plurality of pressure sensors 203 is filtered and amplified by an analog signal processing unit corresponding to an SC3 415, input to the analog input terminal of the A/D converter 451, displayed on the display unit 109, and stored in the RAM 455. The ECG signal and the pulse wave signal stored in the RAM 455 is a digital signal processed by the DSP 453 using a continuous blood pressure analysis program stored in the ROM 457, and the analysis result is displayed on the display unit 109 and stored in a flash memory 459. The stored continuous blood pressure result value can be transmitted to an external device 470, such as a Personal Computer (PC) or a Personal Digital Assistant (PDA), or a server, by using the interface terminal 150, such as an external communication terminal. In order to control the controller 450, external inputs 103 and 105 are used.

Figure 5A:
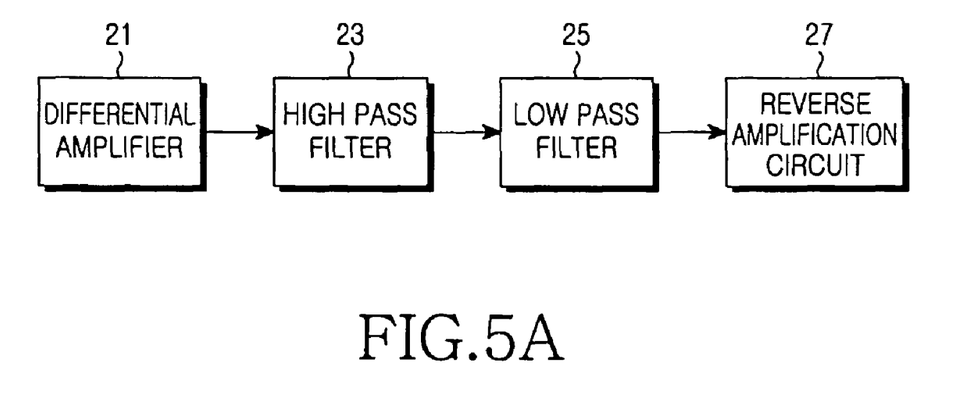
FIGS. 5A, 5B, and 5C are respective circuit diagrams of an analog signal processing unit for processing signals from a pressure sensor, an infrared sensor, and an electrocardiogram (ECG) sensor according to an exemplary embodiment of the present invention.
Figure 5B:
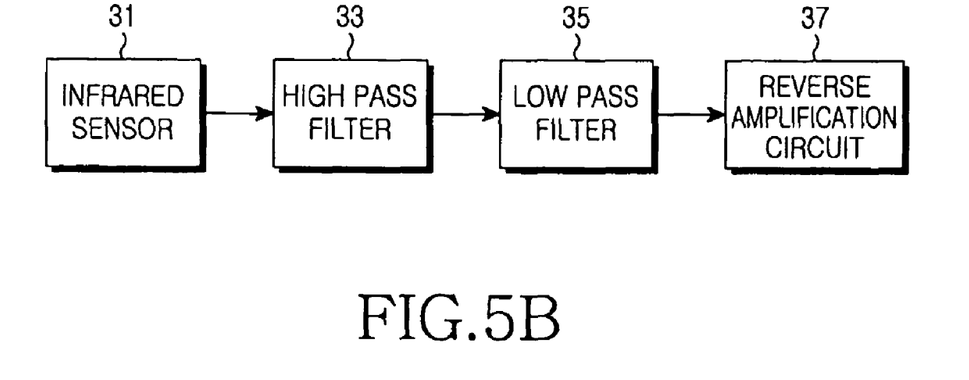
Figure 5C:
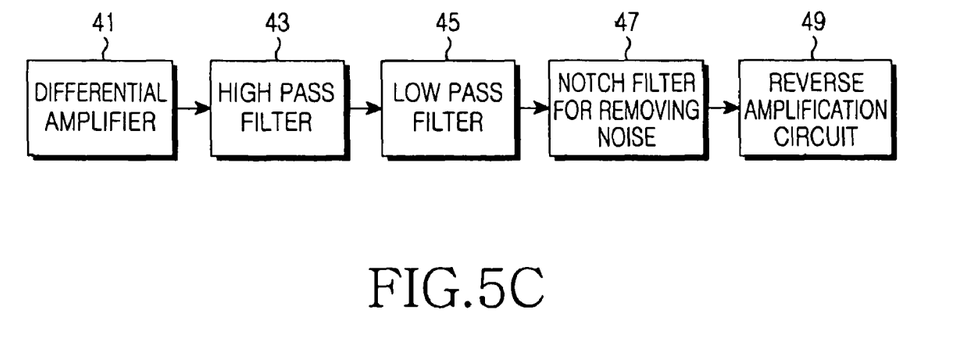

FIGS. 5A, 5B, and 5C are respective diagrams of circuits for processing analog signals measured from the pressure sensor 203, the infrared sensor 202, and the ECG sensor 201 used in the continuous blood pressure measurement apparatus 300 according to an exemplary embodiment of the present invention.

FIG. 5A is a circuit diagram of a unit for processing an analog signal from a pressure sensor according to an exemplary embodiment of the present invention, showing a circuit taking charge of analog signal processing of a pulse wave signal measured by the pressure sensor 203 of the continuous blood pressure and artery elasticity measurement apparatus 300.

Referring now to FIG. 5A, a pulse wave signal having two polarities measured by the pressure sensor (203 of FIG. 4) from the user's wrist 350w is input to the input terminal of the analog signal processing unit (415 of FIG. 4). When the input + signal and − signal are input to a differential amplifier 21, noise components corresponding to the same phases are cancelled, only a difference between the two signals is amplified, and an amplification rate of the differential amplifier 21 is adjusted by a ratio of an input resistor R6 or R9 (R6=R9) to a feedback resistor R4 or R14 (R4=R14). From an initially amplified signal, a signal unnecessary to analyze continuous blood pressure and artery elasticity is removed using a High Pass Filter (HPF) 23, whose cut-off frequency is 0.1 Hz for cutting off low-band noise lower than 0.1 Hz, and a $4^{th}$ order Low Pass Filter (LPF) 25, whose cut-off frequency is 10 Hz for cutting off high-band noise higher than 10 Hz. The noise-cancelled signal is secondary amplified by a reverse amplification circuit 27 not to be saturated higher than a supplied voltage and is input to the analog input terminal of the A/D converter (451 of FIG. 4) of the controller (450 of FIG. 4) in order to be converted to a digital signal.

FIG. 5B is a circuit diagram of a unit for processing an analog signal from an infrared sensor according to an exemplary embodiment of the present invention, showing a circuit taking charge of analog signal processing of an infrared sensor signal measured by the infrared sensor (202 shown in FIG. 4) of the continuous blood pressure measurement apparatus 300.

Referring to FIG. 5B, from the infrared sensor signal measured by the infrared sensor (202 of FIG. 4) from the user's wrist 350w, i.e. an emitter output signal of a photo transistor, a signal unnecessary to analyze artery position information is removed using an HPF 33 whose cut-off frequency is 0.1 Hz for cutting off low-band noise lower than 0.1 Hz and a $4^{th}$ order LPF 35 whose cut-off frequency is 10 Hz for cutting off high-band noise higher than 10 Hz. The noise-cancelled signal is secondary amplified by a reverse amplification circuit 37 not to be saturated higher than a supplied voltage and is input to the analog input terminal of the A/D converter (451 of FIG. 4) of the controller (450 of FIG. 4) in order to be converted to a digital signal.

FIG. 5C is a circuit diagram of a unit for processing an analog signal from an ECG sensor according to another exemplary embodiment of the present invention, showing a circuit taking charge of analog signal processing of an ECG signal measured by the ECG sensor (201 of FIG. 4) of the continuous blood pressure measurement apparatus 300.

Referring to FIG. 5C, an ECG signal is a signal shown by converting an activity potential of a heart measured by three electrodes, i.e. the ECG sensors (201 of FIG. 4), to a voltage, and if a Common Mode Rejection Ratio (CMRR) indicating a ratio of common mode noise input through the human body increases, the common mode noise is removed using a differential amplifier 41, and only a potential difference between a + electrode and a − electrode is amplified. From an initially amplified signal, a signal unnecessary to analyze continuous blood pressure is removed using an HPF 43 whose cut-off frequency is 1 Hz for cutting off low-band noise lower than 1 Hz, a $4^{th}$ order LPF 45 whose cut-off frequency is 30 Hz for cutting off high-band noise higher than 30 Hz, and a notch filter 47 for removing noise due to the general-use frequency (50/60 Hz) input through the electrodes. The noise-cancelled signal is secondary amplified by a reverse amplification circuit 49 not to be saturated higher than a supplied voltage and is input to the analog input terminal of the A/D converter (451 of FIG. 4) of the controller (450 of FIG. 4) in order to be converted to a digital signal.

Figure 6:
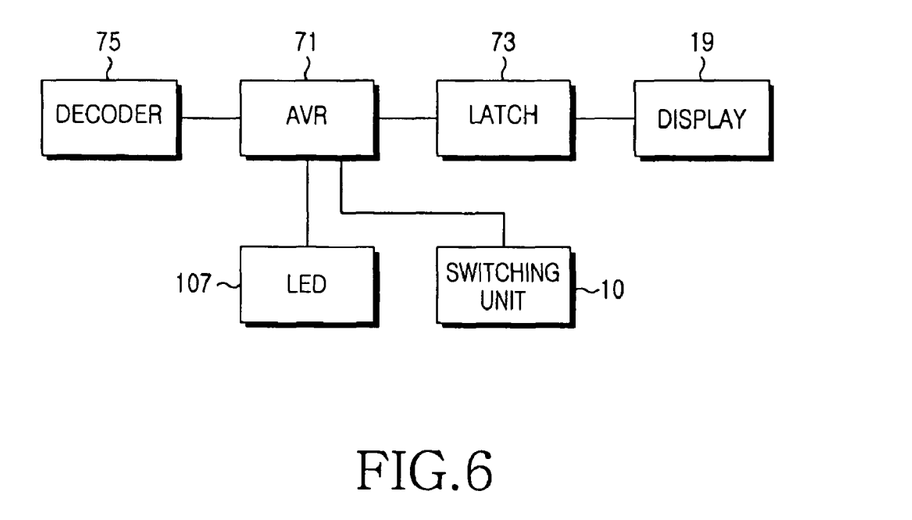
FIG. 6 is a circuit diagram of a controller including an input unit, a state display unit, and a display unit according to an exemplary embodiment of the present invention.

FIG. 6 is a circuit diagram of the controller 450 including an input unit, the state display unit 107, and a display unit 111 in the continuous blood pressure measurement apparatus 300 according to another exemplary embodiment of the present invention.

Referring to FIG. 6, the controller 450 (shown in FIG. 4) in the continuous blood pressure measurement apparatus 300 according to the current exemplary embodiment that includes the display unit 109 of the apparatus 300, the measurement button 101 for measuring measurement in the apparatus 300, the measurement buttons 103 and 105 for external inputs, the state display LED 107 displaying an operating state of the apparatus 300, and the communication terminal 150 for interfacing with the external device 470, such as a PC or PDA.

Analog signal processed pulse wave signal, infrared sensor signal, and ECG signal are input to the analog input terminal of the A/D converter (451 shown in FIG. 4) and converted to digital signals. By performing signal processing of the converted digital signals, the pulse wave signal is displayed on the display unit 109 and stored in the RAM 455 of the controller 450 (shown in FIG. 4). From the stored digital signals, a continuous blood pressure value is deduced using the continuous blood pressure analysis program stored in the ROM (457 in FIG. 4) of the controller 450 and displayed on the display unit 109. Calculated result data is stored in the flash memory 459 of the controller 450 and can be transmitted to the external device 470, such as a cellular phone, via the communication terminal 150. The controller 450 calculates data on an 8-bit basis, has a 16-channel analog input terminal, selects a signal of which an input exists using a multiplexer (MUX) 71, and outputs the selected signal via an output circuit. The equipped A/D converter 451 has 10-bit resolution, and since the controller 450 includes the external communication terminal 150 (shown in FIG. 1), the controller 450 can interface with the external device 470, such as a PC or PDA, without an additional communication interface. The controller 450 also can store the calculation program using the ROM (457 of FIG. 4).

In addition, although the controller 450 can process input data by itself, memory mapping is necessary to expand data storage memory and connect a display Liquid Crystal Display (LCD). In order to perform the memory mapping, address and data buses are preferably be used. However, since an AVR uses an address (16 bits)/data (8 bits) method and uses the same pins as lower address data, data and an address are divided using a latch 73. A data storage memory and an LCD are memory mapped with each other, and in order to generate a chip selecting signal, a digital signal is converted to an analog signal using a decoder 75.

The controller 450 forms a vector component by mixing more than infrared sensor signals using the calculation program stored in the ROM 457, searches for correct position and depth information of an artery using the formed vector component, and can show a continuous blood pressure analysis result by comparing and analyzing a measured pulse wave signal and an ECG signal.

Figure 7:
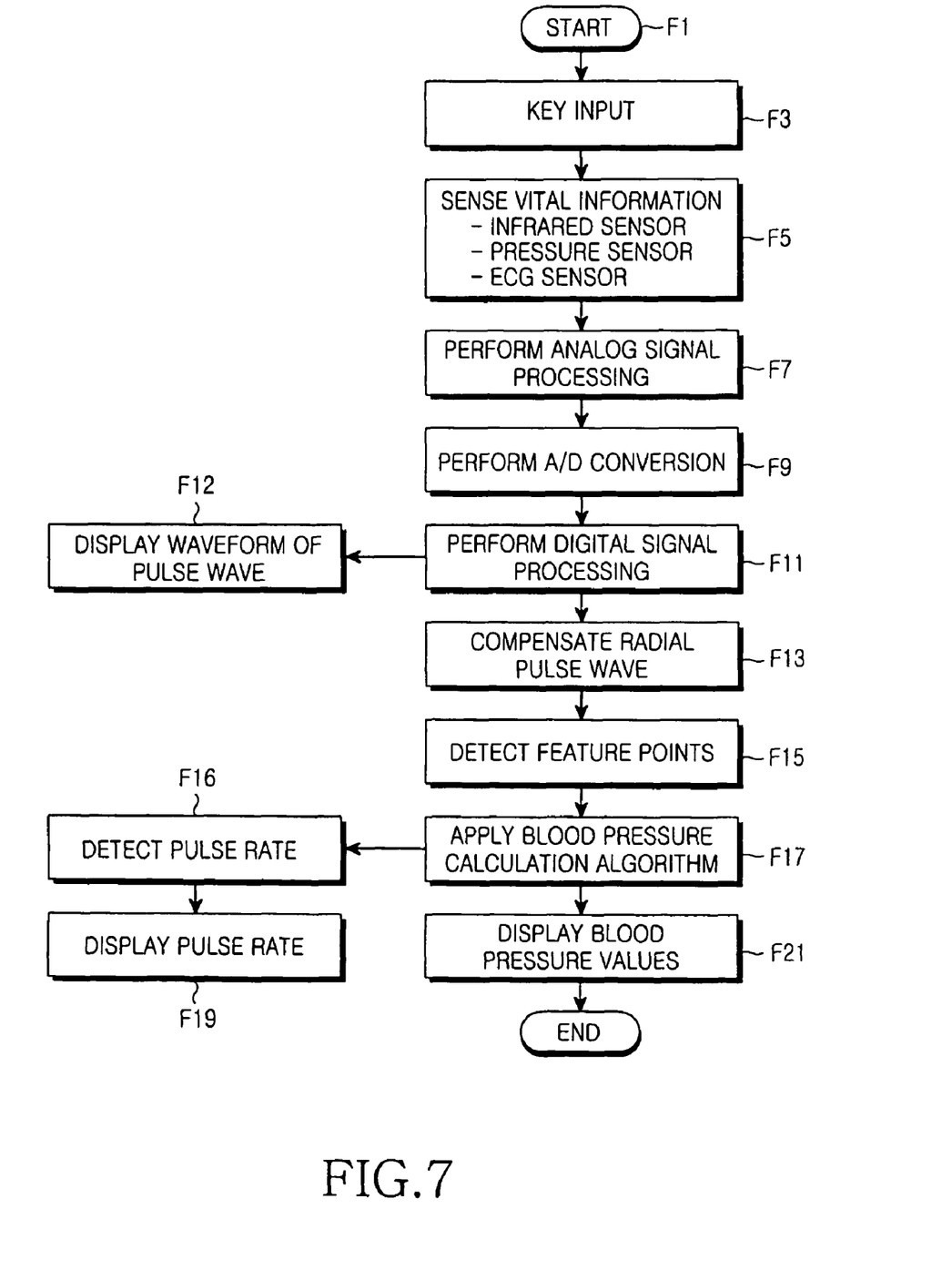
FIG. 7 is a flowchart of a blood pressure measuring method according to an exemplary embodiment of the present invention.

FIG. 7 is a flowchart illustrating exemplary steps of a blood pressure measuring method in the continuous blood pressure measurement apparatus 300 according to an exemplary embodiment of the present invention.

Referring to FIG. 7, when measurement of a pulse wave signal of the user's wrist 350w using the continuous blood pressure measurement apparatus 300 begins in step F1, a signal generated due to the measurement button (101 of FIG. 1) is input to the external inputs (103 and 105 shown in FIG. 4) of the controller (450 shown in FIG. 4) in step F3. By acquiring artery position and depth information using at least one infrared sensor (202 shown in FIG. 4), measuring a pulse wave signal using the pressure sensor (203 shown in FIG. 4), and measuring an ECG signal using the ECG sensor (201 shown in FIG. 4) in step F5, an analog signal processor performs processes the ECG signal, the infrared sensor signal, and the pulse wave signal in step F7. Each one of the analog signal processed ECG signal, infrared sensor signal, and pulse wave signal is input to the analog input terminal of the A/D converter (451 shown in FIG. 4) of the controller (450 shown in FIG. 4) and converted to a digital signal in step F9. Still referring to FIG. 7, a digital LPF is applied to the radial pulse wave signal converted to the digital signal, and after trends are removed in step F11, the radial pulse wave signal is displayed in step F12. By calculating a non-distorted radial artery pressure value from the signal processed radial pulse wave signal using position and depth information from the infrared sensor signal and an R-peak timing of the ECG signal to be described later, variation due to a pressure difference is compensated in step F13, feature points are detected from the compensated radial pulse wave signal in step F15, and an algorithm for calculating a brachial blood pressure value is applied based on the feature points in step F17. A per-minute pulse rate is calculated from the detection of the feature points of the pulse wave in step F16, the calculated pulse rate is displayed in step F19, and a systolic blood pressure value and a diastolic blood pressure value calculated based on the algorithm are displayed in step F21. The algorithm calculation process will be described with reference to FIG. 8A.

Figure 8A:
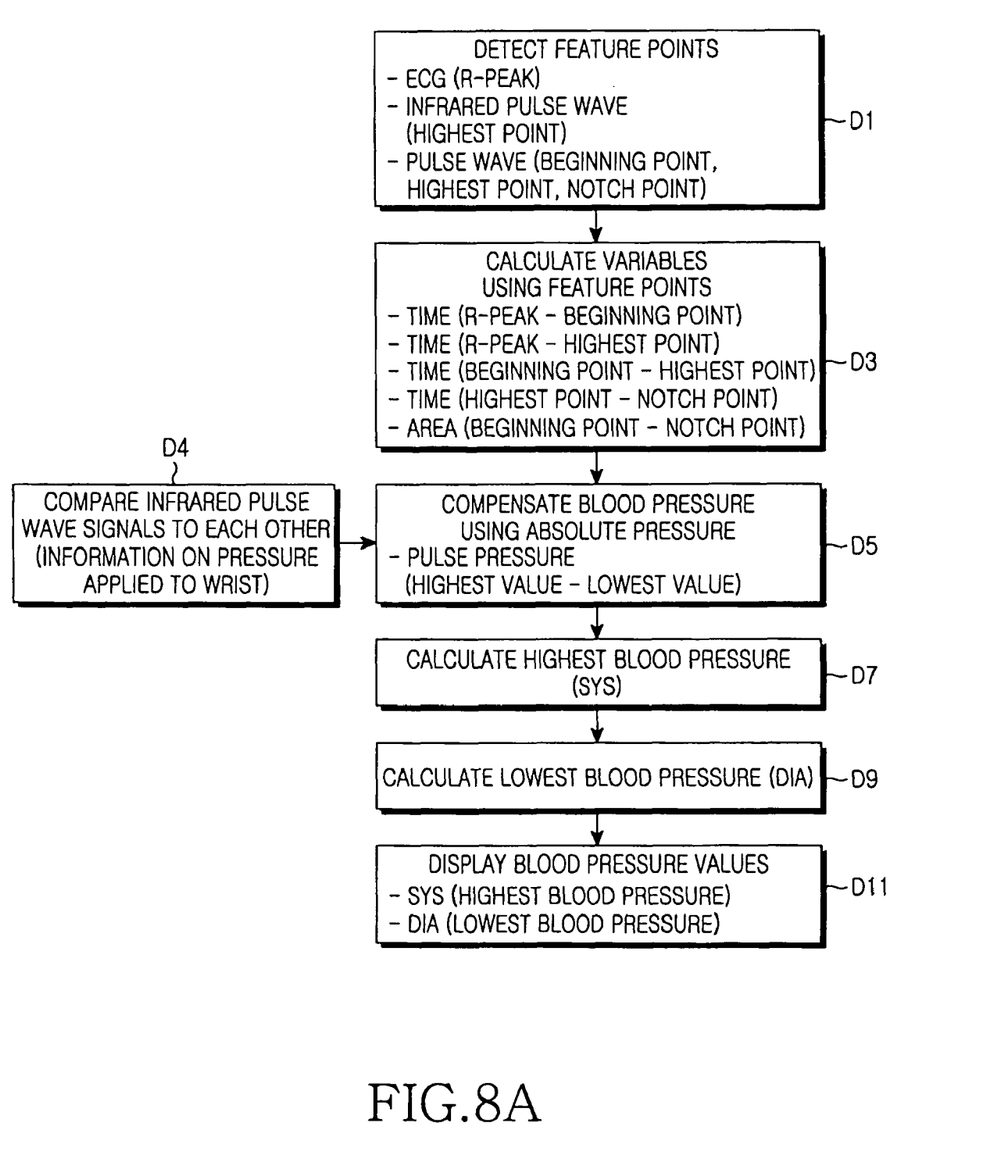
FIG. 8A is a flowchart of a blood pressure measuring method according to an exemplary embodiment of the present invention.

FIG. 8A is a flowchart of a calculation process of the continuous blood pressure measuring algorithm according to an exemplary embodiment of the present invention.

Referring to FIG. 8A, when each feature point is detected in step D1, an R-peak is detected from a P-QRS-T waveform indicating one period of electric activity of a heart using an ECG signal. The R-peak denotes a de-polarization timing of the left ventricle of the heart. A beginning point, the highest point, and a notch point are detected from respective pulse wave signals. A pulse wave signal using infrared is used to compensate the detection of the highest point.

Still referring to FIG. 8A, a linear regression expression correlated to an actual blood pressure value detected through a clinical demonstration using catheters in an actual invasive method using variables calculated using the feature points in step D3, and the highest blood pressure value and the lowest blood pressure value are calculated from the linear regression expression in steps D7 and D9. When the highest blood pressure value and the lowest blood pressure value are finally calculated, the calculation process using the algorithm ends, and the highest blood pressure value and the lowest blood pressure value are then displayed in step D11.

Figure 8B:
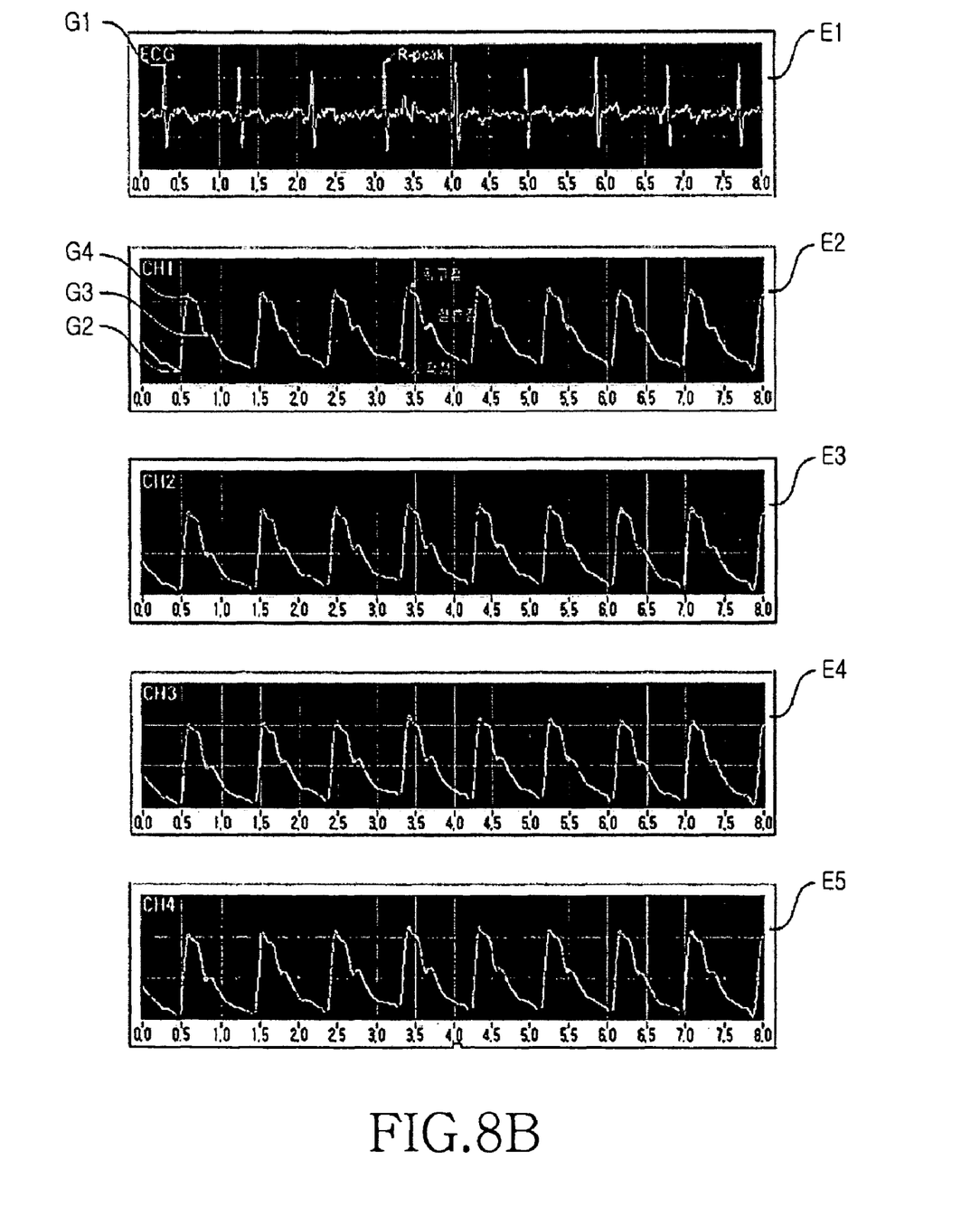
FIG. 8B is a graph of an ECG signal and four pulse waveforms acquired through a clinical demonstration using a device for detecting a blood pressure value of a radial artery according to an exemplary embodiment of the present invention.

FIG. 8B is a graph of an ECG signal E1 and four pulse waveforms E2 through E5 acquired through a clinical demonstration using a device for detecting a blood pressure value of a radial artery according to an exemplary embodiment of the present invention. In the graph illustrated in FIG. 8B, feature points detected by using the blood pressure calculation algorithm described in FIG. 7 are shown.

Referring to FIG. 8B, an R-peak G1 is detected from a P-QRS-T waveform indicating one period of electric activity of a heart from the ECG signal E1. The R-peak G1 denotes a de-polarization timing of the left ventricle of a heart. A beginning point G2, the highest point G4, and a notch point G3 are detected from the respective pulse wave signals E2 through E5.

When the algorithm described in FIG. 8 is applied to these feature points, the highest blood pressure value and the lowest blood pressure value are calculated by calculating the time from the R-peak G1 to the pulse wave beginning point G2, the time from the R-peak G1 to the pulse wave highest point G4, the time from the pulse wave highest point G4 to the pulse wave notch point G3, and an area from the pulse wave beginning point G2 to the pulse wave notch point G3 and expressing a relation to an actual blood pressure value as a linear regression expression.

Figure 9A:
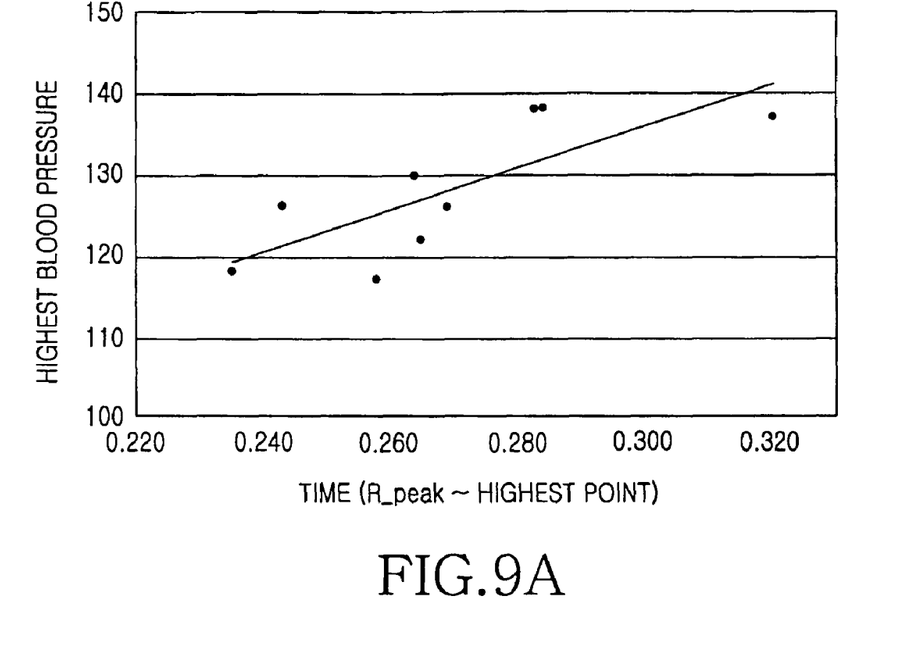
FIGS. 9A, 9B, and 9C are scatter graphs of the lowest blood pressure value, the highest blood pressure value, and a pulse pressure value calculated using a calculation algorithm and actual values obtained from a clinical demonstration according to an exemplary embodiment of the present invention.
Figure 9B:
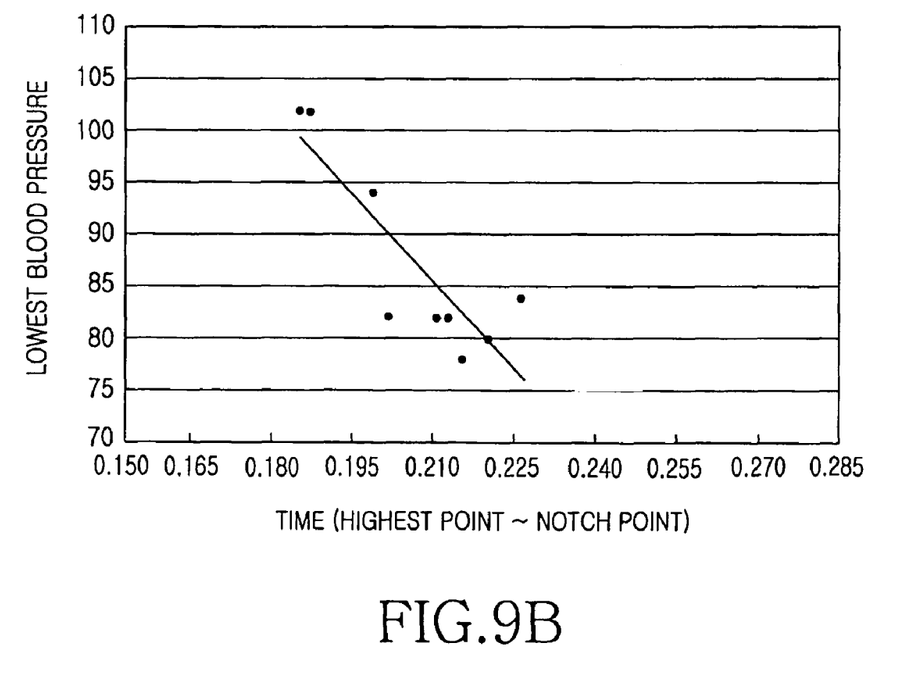
Figure 9C:
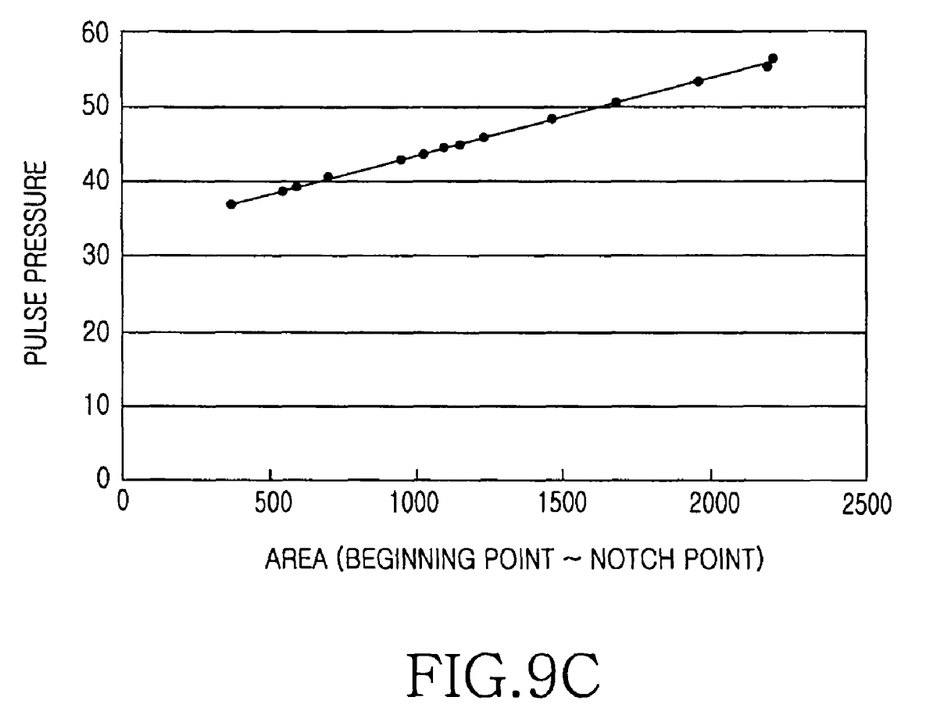

FIGS. 9A, 9B, and 9C are scatter graphs of the lowest blood pressure value, the highest blood pressure value, and a pulse pressure value calculated using the calculation algorithm and actual values obtained from a clinical demonstration according to an exemplary embodiment of the present invention. The showing scatter graphs of representative variables are deduced by applying the algorithm according to an exemplary embodiment of the present invention to the highest blood pressure value and the lowest blood pressure value invasively detected using catheters and the ECG signal E1 and the pulse waveforms E2 through E5 detected by a continuous blood pressure measurement apparatus for clinical validation.

FIG. 9A shows a scatter graph and a linear regression line of a time value from the R-peak G1, which is a variable showing high correlation with the highest blood pressure value among the extracted variables, to the pulse wave highest point G4, FIG. 9B shows a scatter graph and a linear regression line of a time value from the pulse wave highest point G4, which is a variable showing high correlation with the lowest blood pressure value among the extracted variables, to the pulse wave notch point G3, and FIG. 9C shows a scatter graph and a linear regression line of an absolute value of a compensated pulse pressure value, which is used for compensation as an absolute pressure value by setting a criterion of pressure applied to a wrist region using magnitude differences between at least one of the pulse wave signals E2 through E5, and an area value from pulse wave beginning point G2 to the pulse wave notch point G3.

In particular, when the above-described algorithm is summarized, a time difference between an R-peak of an ECG signal and the highest point of a pulse wave has strong correlation with the highest blood pressure, and the time from the highest point of the pulse wave to a notch point has strong correlation with the lowest blood pressure. Since these values are expressed by time, these values are not concerned with measured pressure. In addition, a direct line connecting a beginning point of the pulse wave and the notch point and an area between a waveform of the pulse wave and a direct line connecting a beginning point of the pulse wave and the notch point has strong correlation with pulse pressure indicating a difference between the highest blood pressure and the lowest blood pressure. The three correlation expressions are deduced from a clinical demonstration, and the highest blood pressure, the lowest blood pressure, and mean blood pressure can be obtained from two of the three correlation expressions or a set of any of them.

As described above, according to the present invention, a linear regression expression correlated to an actual blood pressure value detected through a clinical demonstration using the variables (step D3 of FIG. 8A) calculated using the feature points and the pulse pressure (step D5 of FIG. 8A) compensated using absolute blood pressure, and the highest blood pressure (step D7 of FIG. 8A) and the lowest blood pressure (step D9 of FIG. 8A) are finally calculated, and then the calculation process using the algorithm ends, and the highest blood pressure value and the lowest blood pressure value (step D11 of FIG. 8A) are displayed. In addition, the highest and lowest blood pressure values can be transmitted to an external device, such as a nurse's station, network, health monitoring system, etc. periodically and or when the values exceed a predetermined threshold. The threshold could be either higher or lower than a preset range.

As described above, according to the present invention, since a non-invasive continuous blood pressure measurement apparatus, which can be easily used on a person and have portability, and a method thereof can be applied to the development of a system for considerably improving the accuracy of conventional blood pressure measurement apparatuses that do not use a cuff and show quantitative values of accurate blood pressure considering various measurement conditions. Accordingly, the apparatus and method can be positively used for early diagnosis of heart/blood related diseases.

In addition, blood pressure values stored regularly during daily life may be helpful for diagnosis and prescription by being given to a doctor when a user goes to hospital, and excessive substance abuse may be reduced by presenting a planned health care guide based on a trend of variation of blood pressure during one day. Thus, the apparatus can be a requisite health care device in a well-being society. While the invention has been shown and described with reference to a certain preferred exemplary embodiments thereof, it will be understood by those skilled in the art that various changes in form and details may be made therein without departing from the spirit of the invention and the scope of the appended claims.

What is claimed is:

1. A method of cufflessly and non-invasively measuring wrist blood pressure in association with a communication device, the method comprising:
   (a) detecting an electrocardiogram (ECG) using an ECG sensor, detecting infrared pulse waves using an infrared sensor, and detecting pressure pulse wave signals using a pressure sensor, the ECG, infrared pulse waves and pressure pulse waves being detected from a wrist region of a user;
   (b) detecting feature points from the ECG, the infrared pulse waves and the pressure pulse wave signals detected in (a) from the user;
   (c) extracting variables for calculating a highest blood pressure and a lowest blood pressure by applying the feature points detected in step (b) to a blood pressure calculation algorithm; and
   (d) calculating the highest blood pressure and the lowest blood pressure of the user by deducing a scatter diagram using the extracted variables and compensating using absolute pressure to correct a magnitude of a detected pulse after comparing the infrared pulse wave signals to each other to obtain a vector component to search for a measured position and depth of an artery; and
   transmitting the calculated data to a portable communication device.

2. The method of claim 1, wherein the detecting of the feature points from the ECG and pulse wave signals detected from the user in step (b) comprises:
   (i) detecting an R-peak in a P-QRS-T waveform indicating one period of electric activity of a heart from the measured ECG signal; and
   (ii) detecting a beginning point, the highest point, and a notch point of the R-peak,
   wherein R-peak denotes a de-polarization timing of the left ventricle of the heart.

3. The method of claim 2, wherein the calculating of the highest blood pressure and the lowest blood pressure comprises:
   deducing a linear regression expression by using the extracted variables as independent variables; and
   calculating the highest blood pressure and the lowest blood pressure of the user from the deduced linear regression expression.

4. The method according to claim 3, further comprising (e) transmitting the highest and lowest blood pressure values calculated are transmitted to an external device.

5. The method according to claim 3, further comprising (e) storing the highest and lowest blood pressure values from step (d) in a memory.

6. The method according to claim 3, further comprising (e) display the highest and lowest blood pressure values calculated in step (d).

7. The method according to claim 1, wherein the ECG sensor and pressure sensor are integrated in a sensor unit for measuring blood pressure in a wrist region without a cuff.

8. The method according to claim 1, further comprising (e) transmitting the highest and lowest blood pressure values calculated are transmitted to an external device.

9. A method of cufflessly and non-invasively measuring wrist blood pressure in association with a communication device, the method comprising:
 (a) detecting an electrocardiogram (ECG) and pulse wave signals from a wrist region of a user using an ECG sensor and a pressure sensor;
 (b) detecting feature points from the ECG and pulse wave signals detected from the user;
 (c) extracting variables for calculating a highest blood pressure and a lowest blood pressure by applying the feature points detected in step (b) to a blood pressure calculation algorithm; and
 (d) calculating the highest blood pressure and the lowest blood pressure of the user by deducing a scatter diagram using the extracted variables,
 wherein the detecting of the ECG and pulse wave signals in step (a) comprises:
 (i) setting a criterion of pressure applied to the wrist using magnitude differences of the measured more than one pulse wave signals; and
 (ii) compensating for a user environment, including at least one of a position and depth of an artery measured using an infrared sensor, and a criterion value change according to a sensor applied pressure difference.

10. A method of cufflessly and non-invasively measuring wrist blood pressure in association with a communication device, the method comprising:
 (a) detecting an electrocardiogram (ECG) and pulse wave signals from a wrist region of a user using an ECG sensor and a pressure sensor;
 (b) detecting feature points from the ECG and pulse wave signals detected from the user;
 (c) extracting variables for calculating a highest blood pressure and a lowest blood pressure by applying the feature points detected in step (b) to a blood pressure calculation algorithm; and
 (d) calculating the highest blood pressure and the lowest blood pressure of the user by deducing a scatter diagram using the extracted variables,
 wherein the variables for calculating the highest blood pressure and the lowest blood pressure comprises a time value from a detected R-peak of the ECG signal to a pulse wave beginning point, a time value from the R-peak to a pulse wave highest point, a time value from the pulse wave beginning point to a pulse wave highest point, a time value from the pulse wave highest point to a pulse wave notch point, and an area value from the pulse wave beginning point to the pulse wave notch point, and
 the R-peak obtained from the ECG signal is used as a criterion value of time.

11. A method of cufflessly and non-invasively measuring wrist blood pressure in association with a communication device, the method comprising:
 (a) detecting an electrocardiogram (ECG) and pulse wave signals from a wrist region of a user using an ECG sensor and a pressure sensor;
 (b) detecting feature points from the ECG and pulse wave signals detected from the user;
 (c) extracting variables for calculating a highest blood pressure and a lowest blood pressure by applying the feature points detected in step (b) to a blood pressure calculation algorithm; and
 (d) calculating the highest blood pressure and the lowest blood pressure of the user by deducing a scatter diagram using the extracted variables,
 (e) transmitting the highest and lowest blood pressure values calculated are transmitted to an external device;
 wherein the detecting of the feature points from the ECG and pulse wave signals detected from the user in step (b) comprises:
 (i) detecting an R-peak in a P-QRS-T waveform indicating one period of electric activity of a heart from the measured ECG signal; and
 (ii) detecting a beginning point, the highest point, and a notch point of the R-peak,
 wherein R-peak denotes a de-polarization timing of the left ventricle of the heart;
 wherein the calculating of the highest blood pressure and the lowest blood pressure comprises:
 deducing a linear regression expression by using the extracted variables as independent variables; and
 calculating the highest blood pressure and the lowest blood pressure of the user from the deduced linear regression expression, and
 wherein the highest and lowest blood pressure values are transmitted when the values exceed a predetermined threshold value.

* * * * *